US012682981B2

(12) United States Patent
Jin et al.

(10) Patent No.: US 12,682,981 B2
(45) Date of Patent: Jul. 14, 2026

(54) DRUG SCREENING MODEL CONSTRUCTION METHOD, A DRUG SCREENING MODEL CONSTRUCTION DEVICE, A DRUG SCREENING METHOD, APPARATUS AND A MEDIUM

(71) Applicant: Ainnocence Technologies LLC, Miami, FL (US)

(72) Inventors: Yutong Jin, Zhengzhou City (CN); Lurong Pan, Vestavia Hill, AL (US)

(73) Assignee: Ainnocence Technologies LLC

( * ) Notice: Subject to any disclaimer, the term of this patent is extended or adjusted under 35 U.S.C. 154(b) by 576 days.

(21) Appl. No.: 18/173,122

(22) Filed: Feb. 23, 2023

(65) Prior Publication Data

US 2023/0402125 A1     Dec. 14, 2023

(51) Int. Cl.
| | |
|---|---|
| *G16B 15/30* | (2019.01) |
| *G06N 3/04* | (2023.01) |
| *G06N 3/08* | (2023.01) |
| *G16C 20/50* | (2019.01) |
| *G16C 20/70* | (2019.01) |
| *G16C 20/80* | (2019.01) |
| *G16C 10/00* | (2019.01) |
| *G16C 20/30* | (2019.01) |

(52) U.S. Cl.
CPC .............. *G16B 15/30* (2019.02); *G06N 3/04* (2013.01); *G06N 3/08* (2013.01); *G16C 20/50* (2019.02); *G16C 20/70* (2019.02); *G16C 20/80* (2019.02); *G16C 10/00* (2019.02); *G16C 20/30* (2019.02)

(58) Field of Classification Search
CPC ........ G16B 15/30; G16B 20/80; G16B 20/50; G16B 20/70
See application file for complete search history.

(56) References Cited

U.S. PATENT DOCUMENTS

2021/0081804 A1*   3/2021   Stojevic ................... G06N 3/09

FOREIGN PATENT DOCUMENTS

| CN | 109033738 A * 12/2018 ............... G06N 3/08 |
|---|---|
| WO | WO-2019081781 A1 * 5/2019 ......... G06F 16/9024 |

* cited by examiner

*Primary Examiner* — Lam S Nguyen
(74) *Attorney, Agent, or Firm* — Jason C. Cameron

(57) ABSTRACT

A drug screening model construction method and device, a screening method, apparatus and a medium, in the field of drug screening that includes obtaining a drug training set, where the set comprises a chemical formula of a drug protein, a chemical formula of a small molecule and a classification label; drawing an initial graph network of drug protein and small molecule, in which atoms are nodes and chemical bonds are edges connecting nodes; using a random initialization vector to identify the weight vector of each node; reconstructing each node of the initial graph network according to the connection relationship of the initial graph network to obtain a reconstruction network, and repeating the reconstruction steps to obtain at least two layers of reconstruction networks; performing deep learning on the initial graph network and the reconstruction graph network according to the classification labels, and constructing a drug screening model.

9 Claims, 6 Drawing Sheets

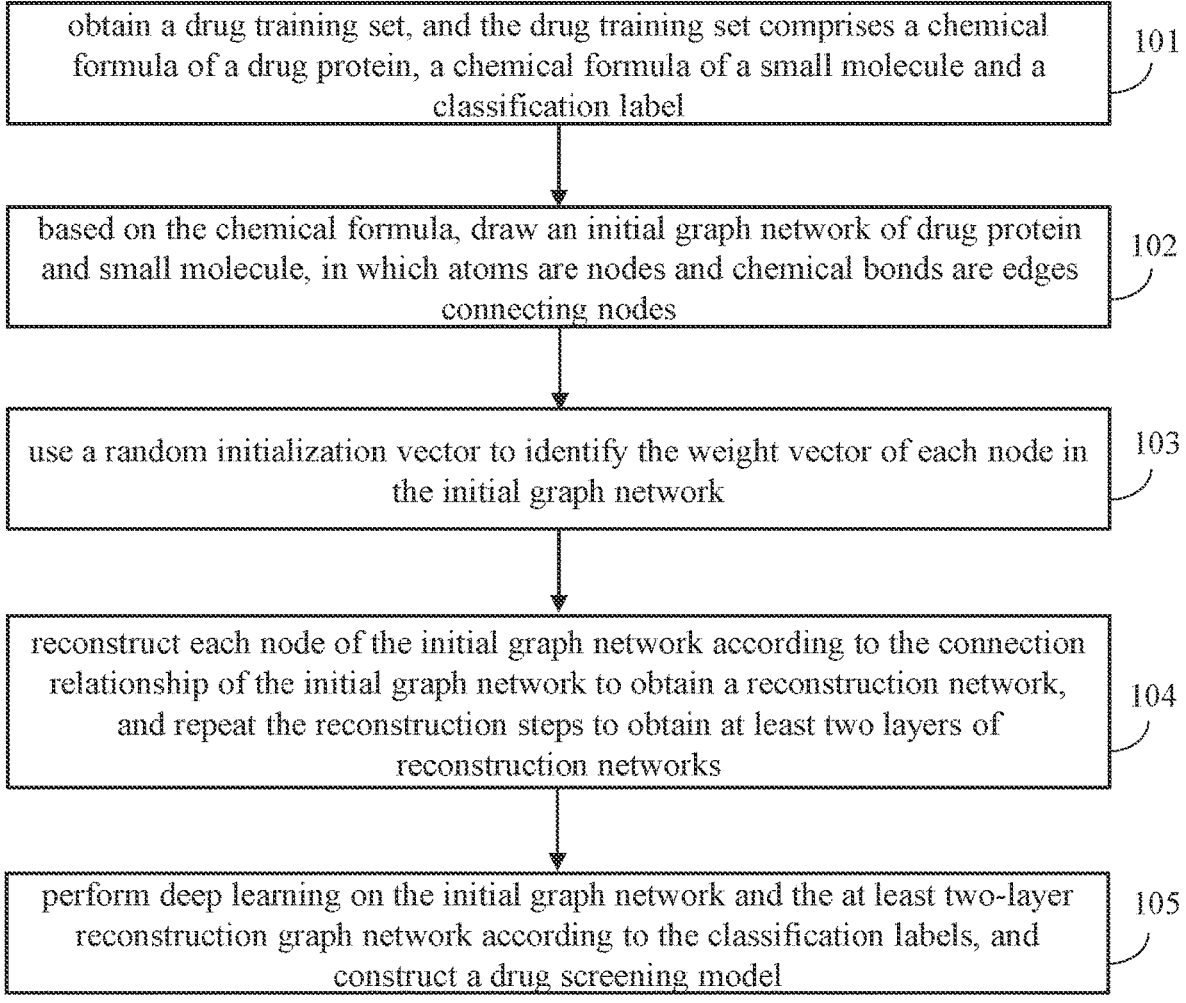

obtain a drug training set, and the drug training set comprises a chemical formula of a drug protein, a chemical formula of a small molecule and a classification label — 101 based on the chemical formula, draw an initial graph network of drug protein and small molecule, in which atoms are nodes and chemical bonds are edges connecting nodes — 102 use a random initialization vector to identify the weight vector of each node in the initial graph network — 103 reconstruct each node of the initial graph network according to the connection relationship of the initial graph network to obtain a reconstruction network, and repeat the reconstruction steps to obtain at least two layers of reconstruction networks — 104 perform deep learning on the initial graph network and the at least two-layer reconstruction graph network according to the classification labels, and construct a drug screening model — 105

FIG. 1

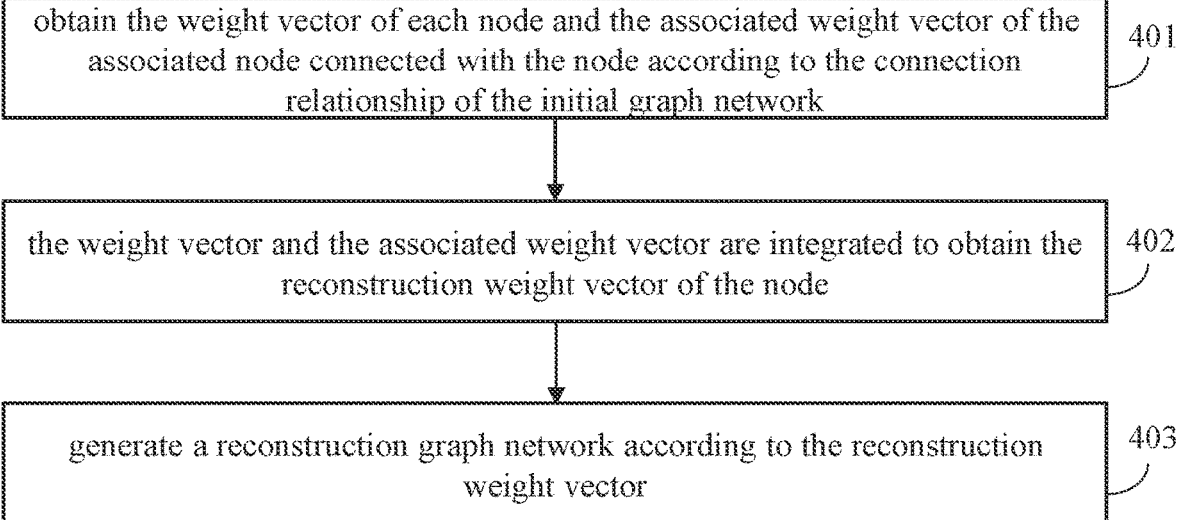

obtain the weight vector of each node and the associated weight vector of the
associated node connected with the node according to the connection
relationship of the initial graph network                                  401 the weight vector and the associated weight vector are integrated to obtain the
reconstruction weight vector of the node                                    402 generate a reconstruction graph network according to the reconstruction
weight vector                                                               403

FIG. 4

DRUG SCREENING MODEL CONSTRUCTION METHOD, A DRUG SCREENING MODEL CONSTRUCTION DEVICE, A DRUG SCREENING METHOD, APPARATUS AND A MEDIUM

CROSS REFERENCE TO RELATED APPLICATIONS

This application claims priority from a patent application filed in China having Patent Application No. 2022106542677 filed on Jun. 10, 2022 and titled "A DRUG SCREENING MODEL CONSTRUCTION METHOD, A DRUG SCREENING MODEL CONSTRUCTION DEVICE, A DRUG SCREENING METHOD, APPARATUS AND A MEDIUM".

TECHNICAL FIELD OF THE INVENTION

The invention relates to the field of drug screening, in particular to a drug screening model construction method, a drug screening model construction device, a drug screening method, apparatus and a medium.

BACKGROUND OF THE INVENTION

Drug discovery has long been a process that consumes a lot of time and money. With the development of computer technology, computational methods are widely used in drug research and development, and virtual drug screening is one of the most valuable technologies. Among them, the virtual screening artificial intelligence method based on protein crystal structure uses the three-dimensional structure information of protein targets to predict the binding situation of proteins and small drug molecules.

The common virtual screening methods based on protein crystal structures often use molecular docking methods. This method uses molecular dynamics and quantum chemistry methods to simulate the process of binding small molecules with proteins, which involves searching for binding sites and using heuristic function calculations. The spatial position of small molecules, etc., consumes a lot of computing power, and there are many possible results, which have certain uncertainties. In addition, proteins are highly flexible. There is a large gap between the conformation and conformation flexibility of the traditional simulation methods based on fixed three-dimensional structure and the real physiological structure proteins, which cannot truly reflect the binding state of proteins and small molecules, resulting in relatively large simulation errors.

Therefore, it is necessary to establish a set of artificial intelligence technology for virtual screening based on protein crystal structure that can surpass the molecular docking method to improve the accuracy and speed of virtual screening.

SUMMARY OF THE INVENTION

Therefore, in order to overcome the above shortcomings of the prior art, the present invention provides a drug screening model construction method, a drug screening model construction device, a drug screening method, apparatus and a medium which can accurately predict the properties of drug compounds in biological and chemical experiments of different scales.

In order to achieve the above object, the present invention provides a drug screening model construction method, which is used for protein crystal structure screening, including: obtain a drug training set, and the drug training set comprises a chemical formula of a drug protein, a chemical formula of a small molecule and a classification label; based on the chemical formula, draw an initial graph network of drug protein and small molecule, in which atoms are nodes and chemical bonds are edges connecting nodes; use a random initialization vector to identify the weight vector of each node in the initial graph network; reconstruct each node of the initial graph network according to the connection relationship of the initial graph network to obtain a reconstruction network, and repeat the reconstruction steps to obtain at least two layers of reconstruction networks; perform deep learning on the initial graph network and the at least two-layer reconstruction graph network according to the classification labels, and construct a drug screening model.

In one embodiment, based on the chemical formula, draw the initial graph network of drug protein and small molecule, which includes: perform molecular docking between drug protein and small molecule based on traditional molecular dynamics to obtain the target molecule; According to the chemical formula of the target molecule, draw the initial graph network of drug protein and small molecule.

In one embodiment, drawing the initial graph network of drug protein and small molecule based on chemical formula includes drawing the initial graph network of drug protein and small molecule based on chemical formula, and the initial graph network at this time includes the initial graph network of drug protein and the initial graph network of small molecule.

In one of the embodiments, using random initialization vector to identify the weight vector of each node in the initial graph network includes: using uniform distribution or normal distribution to select the value of (0, 1) interval to generate initialization vector, and assigning it to the node as its weight vector.

In one of the embodiments, reconstruct each node of the initial graph network according to the connection relationship of the initial graph network to obtain a reconstruction graph network, which includes: obtain the weight vector of each node and the associated weight vector of the associated node connected with the node according to the connection relationship of the initial graph network; integrate the weight vector with the associated weight vector to obtain the reconstruction weight vector of the node; generate the reconstruction graph network according to the reconstruction weight vector.

In one of the embodiments, perform deep learning on the initial graph network and the at least two-layer reconstruction graph network according to the classification labels, and construct the drug screening model, includes: respectively extract features of the initial graph network and at least two layers of the reconstruction graph network to obtain the hierarchical network features; according to the classification labels, the deep learning network is used to learn the hierarchical network features, and construct a drug screening model.

In one of the embodiments, perform the feature extraction on the initial graph network and the at least two-layer reconstruction graph network, respectively, to obtain hierarchical network features, including: feature extraction is performed on the initial graph network and at least two layers of reconstruction graph networks by functions to obtain function vector features; the function vector features are normalized in the probability space to obtain hierarchical network features.

A drug screening method, including: drawing a target initial graph network based on the chemical formula of the target protein and small molecule, in which atoms are nodes and chemical bonds are edges connecting the nodes; input the target initial graph network into the drug screening model, and output the analysis result of the target protein and small molecule, wherein the drug screening model is trained by the above method.

A drug screening model reconstruction device, which includes: a training set acquisition module, used to acquire a drug training set, wherein the drug training set includes a chemical formula of the target protein, a chemical formula of small molecule and a classification label; a graph network drawing module, used to draw an initial graph network based on the chemical formula, in which atoms are nodes and chemical bonds are edges connecting nodes; a vector identification module, used to identify the weight vector of each node in the initial graph network by using a random initialization vector; a reconstruction module, used to reconstruct each node of the initial graph network according to the connection relationship of the initial graph network to obtain a reconstruction graph network, and repeating the reconstruction steps to obtain at least two layers of reconstruction networks, and a model training module, used for deeply learning the initial graph network and at least two layers of reconstruction graph networks according to the classification labels, and construct a drug screening model.

A computer device comprises a memory and a processor, wherein the memory stores a computer program, and is characterized in that the processor implements the steps of the above method when executing the computer program.

A computer readable storage medium, on which a computer program is stored, is characterized in that when a processor execute the computer program, implementing the steps of the above method.

Compared with the prior art, the present invention has the advantages that by modeling and analyzing the initial graph network corresponding to a chemical formula of a drug protein and a chemical formula of a small molecule, and adopting the initial graph network and the reconstruction graph network in modeling instead of the traditional mode based on molecular fingerprint (Fingerprint), can identify two different graph networks of the same drug only by machine learning, which can not only effectively reduce artificial feature design, but also expand the coverage of features, improve efficiency and accuracy, And by using big data and deep learning methods, greatly save the computational consumption of molecular dynamics, quantum mechanics, quantum chemistry, etc., and greatly improve the computational speed. The present invention can take into account the high flexibility of the protein, and the simulation mode based on the elastic graph neural network can better simulate the flexibility characteristics of protein, and can more accurately predict the properties of compounds in biological and chemical experiments of different scales.

BRIEF DESCRIPTION OF DRAWINGS

In order to illustrate the technical solutions of the embodiments of the present application more clearly, the following briefly introduces the drawings that are used in the embodiments. Obviously, the drawings in the following description are only some embodiments of the present application, and for persons skilled in the art, other drawings may also be obtained according to the drawings without any creative efforts.

FIG. 1 is a schematic flowchart of a drug screening model construction method in an embodiment of the present invention;

FIG. 4 is a schematic flowchart of a reconstruction step in an embodiment of the present invention;

DETAILED DESCRIPTION

Figure 2:
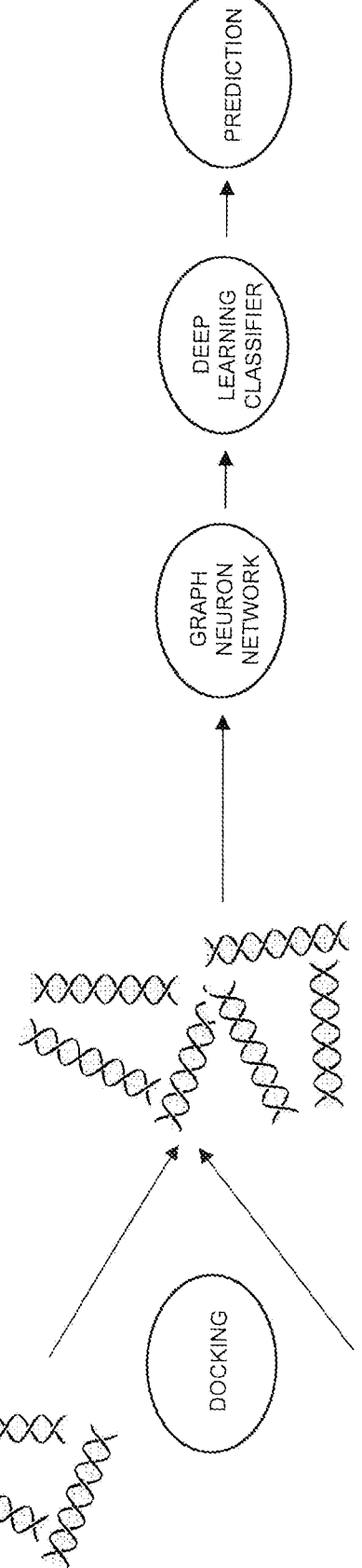
FIG. 2 is a schematic flowchart of a drug screening model construction method in the embodiment of the present invention.

The embodiments of the present disclosure are described in detail below with reference to the drawings. The embodiments of the present disclosure are described below by way of specific examples, and those skilled in the art can easily understand other advantages and effects of the present disclosure from the contents disclosed in this specification. Obviously, the described embodiments are only a part of the embodiments of the present disclosure, but not all of the embodiments. The present disclosure may be implemented or applied by different other embodiment, and that details of the present specification may be modified or changed from various aspect and applications without departing from the spirit of the present application. It should be noted that the following embodiments and the features in the embodiments can be combined with each other without conflict. Based on the embodiments in the present disclosure, all other embodiments obtained by persons of ordinary skill in the art without creative work are within the scope of the protection of the present disclosure.

It should be noted that various aspects of embodiments within the scope of the appended claims are described below. It should be apparent that the aspects described herein may be embodied in a wide variety of forms, and that any specific structures and/or functions described herein are merely illustrative. Based on the present application, persons skilled in the art will appreciate that one aspect described herein may be implemented independently of any other aspect and that two or more of these aspects may be combined in various ways. For example, any number and aspects set forth herein may be used to implement an apparatus and/or practice a method. In addition, the apparatus may be implemented and/or the method practiced using other structures and/or functionalities in addition to one or more of the aspects set forth herein.

It is to be noted that, various aspects of embodiments within the scope of the appended claims are described below. It is obvious that the aspects described herein can be embodied in a wide variety of forms, and any specific structures and/or functions described herein are illustrative only. Based on this disclosure, persons skilled in the art should understand that one aspect described herein can be implemented independently of any other aspect, and two or more of these aspects can be combined in various ways. For example, any number of aspects set forth herein can be used to implement devices and/or practice methods. In addition, other structures and/or functionalities other than one or more of the aspects set forth herein can be used to implement this device and/or practice this method.

Furthermore, details in the following description are for a purpose of a thorough understanding of the embodiments. However, it is to be understood by those skilled in the art that an aspect of the disclosure may be practiced without these details.

As shown in FIG. 1, an embodiment of the present disclosure provides a screening model construction method, which can be applied to a terminal or a server. The terminal can be but not limited to various personal computers, notebook computers, smart phones, tablet computers and portable intelligent devices, and the server can be realized by an independent server or a server cluster composed of multiple servers. The method includes the following steps:

Step 101, obtain a drug training set, and the drug training set comprises a chemical formula of a drug protein, a chemical formula of a small molecule and a classification label.

The server can obtain a drug training set, and the drug training set contains the chemical formula of drug protein, the chemical formula of small molecule and the classification label. The drug protein in the drug training set be already validated drug. For example, the drug protein is a protein part with a protein-ligand co-crystal structure, which is queried and sorted through pdb (protein three-dimensional structure data file) database. Small molecule is a small molecule compound with the experimental record of enzyme activity in protein in pdb database. The classification label can be words or letters that describe the properties of the drug, such as the content related to the drug efficacy.

Step 102, based on the chemical formula, draw an initial graph network of drug protein and small molecule, in which atoms are nodes and chemical bonds are edges connecting nodes.

The server based on the chemical formula draws an initial graph network, in which the atoms are nodes and the chemical bonds are the edges connecting the nodes. When there is a chemical bond between two atoms, whether the bond is a single, a double bond or a triple bond, it is drawn as an edge. The initial graph network can be a set of functions organized in a topological space according to graph structure for relational reasoning. The graph structure can be composed of two sets: Node set (Node) and Edge set (Edge), where the edge set describes how nodes are connected to each other.

In one embodiment, based on the chemical formula, draw the initial graph network of drug protein and small molecule, which includes: perform molecular docking between drug protein and small molecule based on traditional molecular dynamics to obtain the target molecule; According to the chemical formula of the target molecule, draw the initial graph network of drug protein and small molecule. As shown in FIG. 2, the server can perform molecular docking between drug protein and small molecules based on traditional molecular dynamics, and draw the docked target molecules to obtain an initial graph network.

Figure 3:
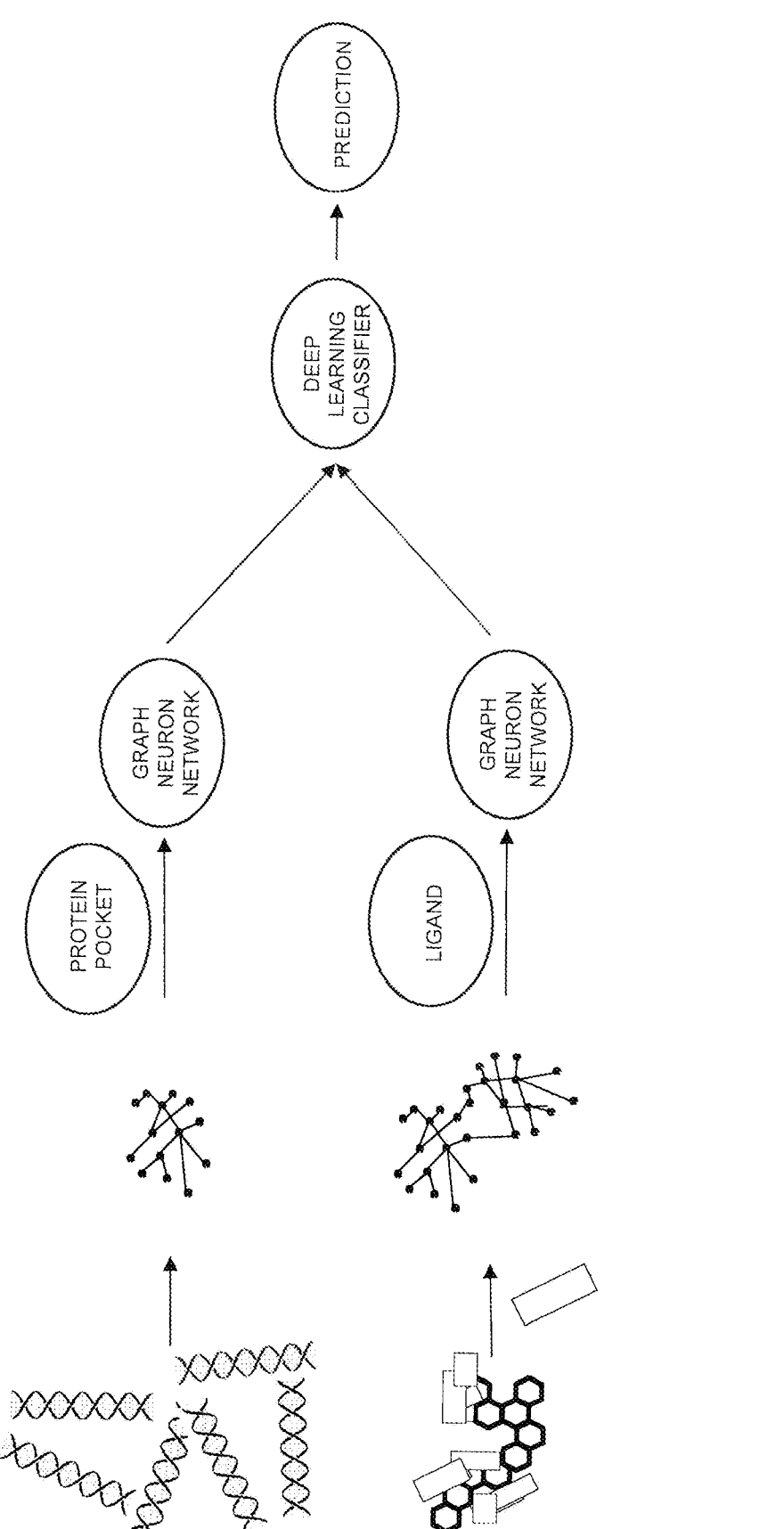
FIG. 3 is a schematic flowchart of a drug screening model construction method in an embodiment of the present invention.

In one embodiment, drawing the initial graph network of drug protein and small molecule based on chemical formula includes drawing the initial graph network of drug protein and small molecule based on chemical formula, and the initial graph network at this time includes the initial graph network of drug protein and the initial graph network of small molecule. As shown in FIG. 3, the server can also draw the initial graph network of drug protein and small molecule based on the chemical formula, and the initial graph network at this time includes the initial graph network of drug protein and the initial graph network of small molecule.

Step 103, use a random initialization vector to identify the weight vector of each node in the initial graph network. The server uses random initialization vector to identify the weight vector of each node in the initial graph network. The server can randomly generate the weight value of any edge, and then assign the corresponding weight vector to each node according to the generated weight value. In one of the embodiments, using random initialization vector to identify the weight vector of each node in the initial graph network includes: using uniform distribution or normal distribution to select the value of (0, 1) interval to generate initialization vector, and assigning it to the node as its weight vector. For example, the server can assign the weight value to each edge in a uniform distribution way, and then assign the corresponding weight vector to each node according to the generated weight value. Uniform distribution means that each value in the pointing quantity is distributed in the interval of (0, 1) with equal probability. Normal distribution refers to each value of the vector is normally distribution in the interval of (0, 1).

Step 104, reconstruct each node of the initial graph network according to the connection relationship of the initial graph network to obtain a reconstruction network, and repeat the reconstruction steps to obtain at least two layers of reconstruction networks. The server reconstructs each node of the initial graph network according to the connection relationship of the initial graph network to obtain a reconstruction graph network, and repeat the reconstruction steps to obtain at least two layers of reconstruction graph networks. Preferably, the number of layers of the server reconstruction graph network is 3 to 6 layers. The server repeats the reconstruction steps each time based on the newly-constructed reconstruction graph network, so each reconstruction graph network is different, and the information contained in each node is gradually enriched.

Step 105, perform deep learning on the initial graph network and the at least two-layer reconstruction graph network according to the classification labels, and construct a drug screening model. The server performs deep learning on the initial graph network and the at least two-layer reconstruction graph network according to the classification labels, and constructs a drug screening model. The deep learning network can be BP neural network (Back Propagation), convolutional network, neural network, etc. The server determines the network features in the initial graph network and the at least two-layer reconstruction graph network through the learning network, and the network features are trained to correspond to the classification labels to construct and obtain a drug screening model.

In the above method, the initial graph network corresponding to the chemical formula of protein and the chemical formula of small molecule is modeled and analyzed, and the initial graph network and the reconstruction graph network are adopted in modeling instead of the traditional method based on molecular fingerprint (Fingerprint), and only two different graph networks of the same drug are identified by machine learning, which can not only effectively reduce artificial feature design, but also expand the coverage of features, improve efficiency and accuracy, and greatly save molecular dynamics, quantum mechanics and quantum learning by using big data and deep learning methods. The invention can better simulate the structural diversity of small molecules in different physiological environments, and accurately predict the properties of compounds in biological and chemical experiments of different scales.

As shown in FIG. 4, in one embodiment, reconstruct each node of the initial graph network according to the connection relationship of the initial graph network to obtain a reconstruction graph network, which includes the following steps:

Step 401, obtain the weight vector of each node and the associated weight vector of the associated node connected with the node according to the connection relationship of the initial graph network. The server obtains the weight vector of each node and an associated weight vector of the associated node connected with the node according to the connection relationship of the initial graph network.

Step 402, the weight vector and the associated weight vector are integrated to obtain the reconstruction weight vector of the node. The server integrates the weight vector and the associated weight vector to obtain the reconstruction weight vector of the node. In one embodiment, the integration formula is, where is the set of nodes connecting all nodes i, vi is the $i^{th}$ node, i, j are the node numbers, is the vector of the nodes numbered i and j in the kth layer network, and is the vector of the edge, $f_k$ is the $k^{th}$ layer network.

Step 403, generate a reconstruction graph network according to the reconstruction weight vector. The server generates a reconstruction graph network according to the reconstruction weight vector.

In one embodiment, the initial graph network and at least two layers of reconstruction graph networks are deeply learned according to the classification labels, and construct a drug screening model, which includes: respectively extracting the features of the initial graph network and the at least two layers of reconstruction graph networks to obtain hierarchical network features; According to the classification label, a deep learning network is adopted to learn the hierarchical network characteristics, and construct a drug screening model.

The server performs feature extraction on the initial graph network and the at least two-layer reconstruction graph network, respectively, to obtain hierarchical network features. In one embodiment, the server may extract the picture features of the initial graph network and the reconstruction graph network respectively, and analyze the picture details in the graph network. In one embodiment, the server may extract the vector features of the initial graph network and the reconstruction graph network respectively, and then analyze the graph network. Specifically, the server can follow the formula, where R is the readout function (feature read function). The server can select vector features by adding and averaging.

In one of the embodiments, feature extraction is performed on the initial graph network and the at least two-layer reconstruction graph network respectively to obtain hierarchical network features, including: performing feature extraction on the initial graph network and the at least two layers of the reconstruction graph network respectively through a function to obtain function vector features; The function vector features are normalized in probability space to obtain hierarchical network features.

The server performs feature extraction on the initial graph network and the at least two-layer reconstruction graph network respectively through functions to obtain function vector features. The server obtains the function vector feature according to the formula. where R is the readout function (feature read function). The server selects vector features by taking an average. The server normalizes the function vector features in the probability space to obtain hierarchical network features. The server can take the softmax function as a direct function of the classifier and compute the normalization operation in the probability space. The specific mathematical formula of the softmax function is, and its function is to normalize the calculated result from the entire real number field to the (0, 1) interval, thereby representing the probability between each node.

The above method only retains the most core compound information (such as atomic number, single or double bonds and other node or edge information) as the connected atom information, so that model training can be completed more efficiently and high-quality models can be extracted.

The application also provides a drug screening method, including: drawing a target initial graph network based on the chemical formula of the target protein and small molecule, in which atoms are nodes and chemical bonds are edges connecting the nodes; input the target initial graph network into the drug screening model, and output the analysis result of the target protein and small molecule, wherein the drug screening model is trained by the above method.

Figure 5:
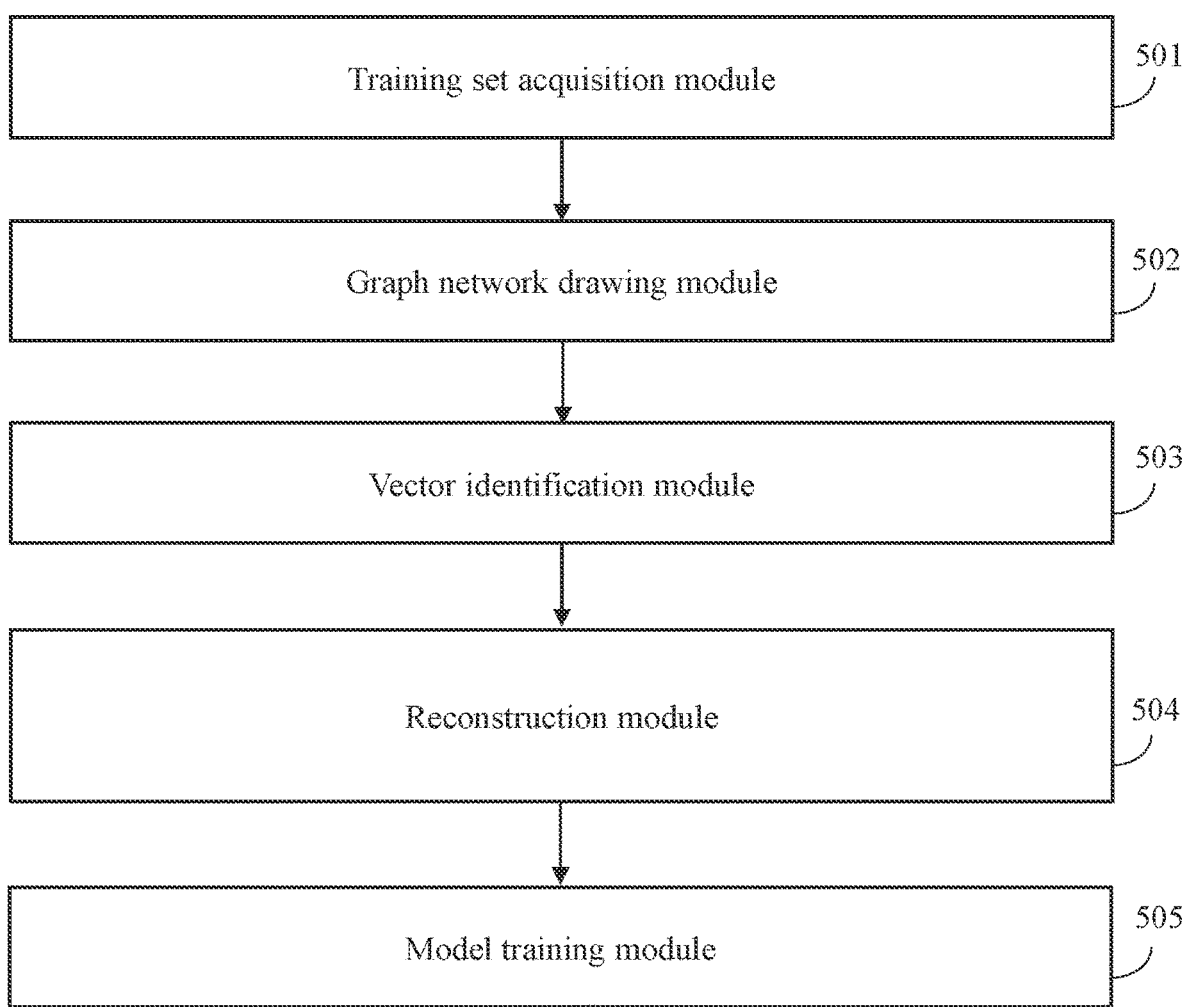
FIG. 5 is a structural block diagram of a drug screening model construction device in an embodiment of the present invention.

In one embodiment, as shown in FIG. 5, a drug screening model construction device is provided, which includes a training set acquisition module 501, a graph network drawing module 502, a vector identification module 503, a reconstruction module 504 and a model training module 505.

A training set acquisition module 501, configured to acquire a drug training set, wherein the drug training set includes a chemical formula of the target protein, a chemical formula of small molecule and a classification label. The graph network drawing module 502 is used to draw an initial graph network based on the chemical formula, in which atoms are nodes and chemical bonds are edges connecting nodes. The vector identification module 503 is configured to identify the weight vector of each node in the initial graph network by using a random initialization vector.

The reconstruction module 504 is used to reconstruct each node of the initial graph network according to the connection relationship of the initial graph network to obtain a reconstruction graph network, and repeating the reconstruction steps to obtain at least two layers of reconstruction networks. The model training module 505 is used for deeply learning the initial graph network and at least two layers of reconstruction graph networks according to the classification labels, and construct a drug screening model. In one of the embodiments, the graph network drawing module includes:

The molecular docking unit is used for molecular docking between drug proteins and small molecules based on traditional molecular dynamics to obtain target molecules. The graph network drawing unit is used to draw the initial graph network of drug proteins and small molecules according to the chemical formula of the target molecule.

In one of the embodiments, the graph network drawing module includes:

The graph network drawing unit is used to draw the initial graph network of the drug protein and the small molecule based on the chemical formula. The initial graph network at this time includes the initial graph network of the drug protein and the initial graph network of the small molecule.

In one embodiment, the vector identification module includes:

The vector identification unit is used to select values in the (0, 1) interval using uniform distribution or normal distribution to generate an initialization vector, and assign it to nodes as its weight vector.

In one embodiment, the reconstruction module 504 includes:

The weight vector obtaining unit is used to obtain the weight vector of each node and the associated weight vector of the associated node connected to the node according to the connection relationship of the initial graph network.

The integration unit is used to integrate the weight vector and the associated weight vector to obtain the reconstruction weight vector of the node.

The reconstruction unit is used to generate a reconstruction graph network according to the reconstruction weight vector.

In one of the embodiments, the model training module includes:

The feature extraction unit is used to respectively extract features of the initial graph network and at least two layers of reconstruction graph networks to obtain hierarchical network features. The model building unit is used to learn hierarchical network characteristics by adopting deep learning network according to the classification labels, and building a drug screening model.

In one of the embodiments, the model training module includes:

The vector extraction unit is used to respectively extract the features of the initial graph network and the at least two layers of reconstruction graph networks through functions to obtain the function vector features. The normalization unit is used to normalize the feature of the function vector in the probability space to obtain the hierarchical network feature.

In one embodiment, a drug screening device is provided, which includes a graph network drawing module and a drug analysis module. The graph network drawing module is used to draw a target initial graph network based on the chemical formula of the target protein and small molecule, in which atoms are nodes and chemical bonds are edges connecting the nodes. The drug analysis module is used to input the target initial graph network into the drug screening model and output the analysis result of the target drug, wherein the drug screening model is obtained by training by the above method.

Figure 6:
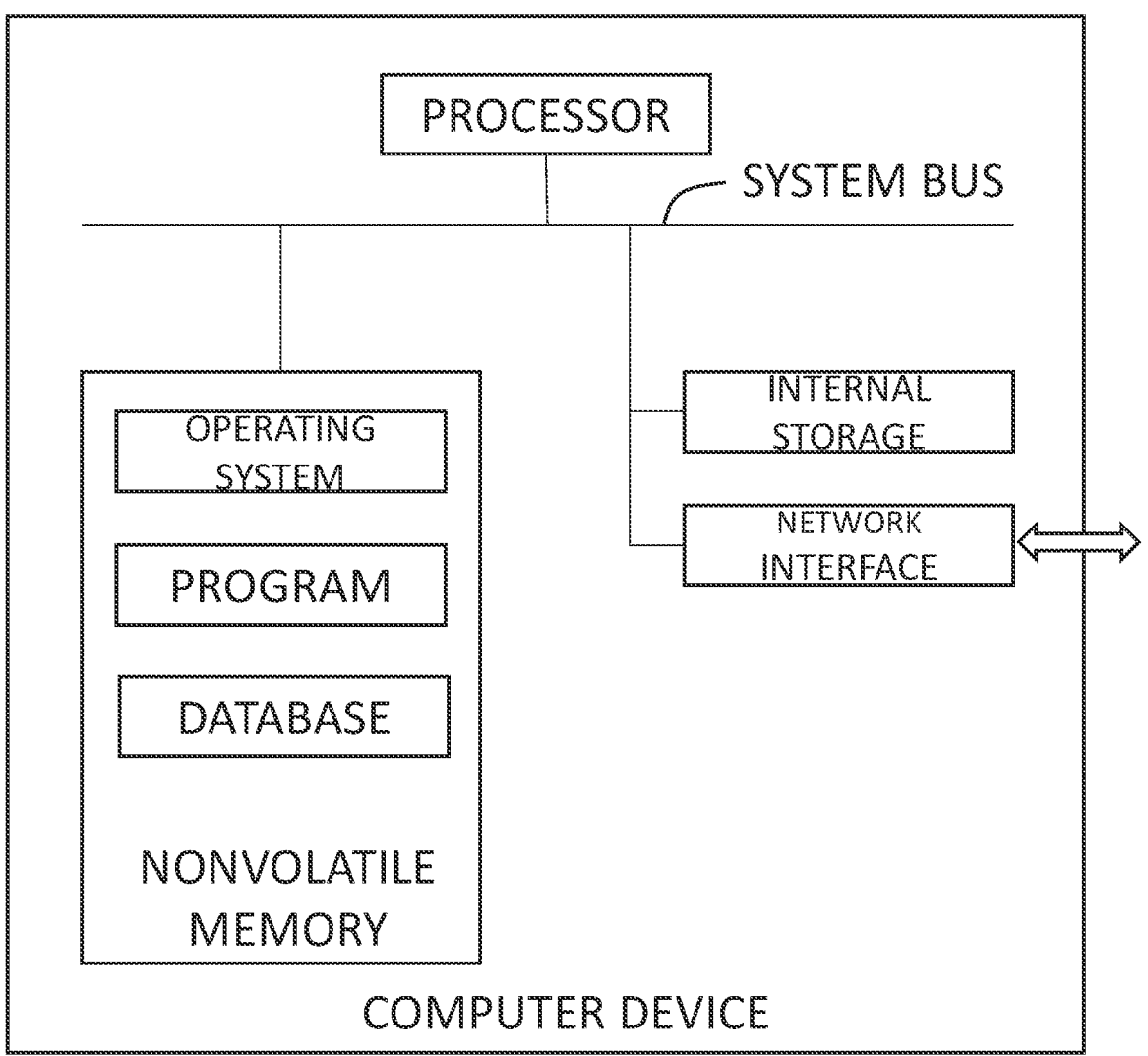
FIG. 6 is an internal structure diagram of a computer device in an embodiment of the present invention.

In one embodiment, a computer device is provided, and the computer device may be a server, and its internal structure diagram may be as shown in FIG. 6. The computer device includes a processor, memory, a network interface, and a database connected by a system bus. Wherein, the processor of the computer device is used to provide computing and control capabilities. The memory of the computer device includes a nonvolatile storage medium, an internal memory. The nonvolatile storage medium stores an operating system, a computer program, and a database. The internal memory provides an environment for the operation of the operating system and computer programs in the non-volatile storage medium. The database of the computer device is used to store data such as a drug training set or a drug screening model. The network interface of the computer device is used to communicate with an external terminal through a network connection. The computer program, when executed by the processor, realizes a drug screening model construction method or a drug screening method.

In one embodiment, a computer device is provided, including a memory and a processor, the memory stores a computer program, and when the processor executes the computer program, the processor implements the following steps: obtain a drug training set, where the drug training set includes the chemical formula of the drug protein, the chemical formula of the small molecule, and classification label; based on drug chemical formula, draw an initial graph network, in which atoms are nodes, and chemical bonds are edges connecting nodes; random initialization vector is used to identify the weight of each node in the initial graph network vector; reconstruct each node of the initial graph network according to the connection relationship of the initial graph network to obtain a reconstruction graph network, and repeat the reconstruction steps to obtain at least two layers of reconstruction graph networks; according to the classification labels, the initial graph network and at least a two-layer reconstruction graph network are deep learned, and construct a drug screening model.

In one embodiment, when the processor executes the computer program, the initial graph network for drawing the drug protein and the small molecule based on the chemical formula includes: performing molecular docking between the drug protein and the small molecule based on traditional molecular dynamics to obtain the target molecule; based on the chemical formulas of target molecules, draw initial graph networks of drug proteins and small molecule.

In one embodiment, when the processor executes the computer program, the initial graph network for drawing the drug protein and the small molecule based on the chemical formula includes: based on the chemical formula, draw the initial graph network for the drug protein and the small molecule respectively, and the initial graph at this time is the network contains an initial graph network for drug proteins and an initial graph network for small molecule.

In one embodiment, when the processor executes the computer program, using a random initialization vector to identify the weight vector of each node in the initial graph network includes: select the value of (0, 1) interval by uniform distribution or normal distribution to generate the initialization vector, and assign it to the node as its weight vector.

In one embodiment, when a processor executes a computer program, reconstructing each node of the initial graph network according to the connection relationship of the initial graph network to obtain a reconstruction graph network, which includes: obtain the weight vector of each node and the associated weight vector of the associated node connected with the node according to the connection relationship of the initial graph network; integrate the weight vector with the associated weight vector to obtain the reconstruction weight vector of the node; generate the reconstruction graph network according to the reconstruction weight vector.

In one embodiment, when the processor executes the computer program, performing deep learning on the initial graph network and the at least two-layer reconstruction graph network according to the classification labels, and constructing the drug screening model, includes: respectively extract features of the initial graph network and at least two layers of the reconstruction graph network to obtain the hierarchical network features; according to the classification labels, the deep learning network is used to learn the hierarchical network features, and construct a drug screening model.

In one embodiment, when the processor executes the computer program, the feature extraction is performed on the initial graph network and the at least two-layer reconstruction graph network, respectively, to obtain hierarchical network features, including: feature extraction is performed on the initial graph network and at least two layers of reconstruction graph networks by functions to obtain function vector features; the function vector features are normalized in the probability space to obtain hierarchical network features.

In one embodiment, a computer device is provided, including a memory and a processor, the memory stores a computer program, and the processor implements the following steps when executing the computer program: drawing initial graph network based on the chemical formula of the target protein and small molecule, the atoms in the initial graph network are nodes, and the chemical bonds are the edges connecting the nodes; input the target initial graph network into the drug screening model, and output the analysis results of the target protein and small molecule, wherein the drug screening model is obtained by training by the above-mentioned method.

In one embodiment, a computer-readable storage medium is provided, on which a computer program is stored, and when the computer program is executed by a processor, the following steps are implemented: obtain a drug training set, where the drug training set includes the chemical formula of the target protein, the chemical formula of small molecule, and classification label; based on the drug chemical formula, draw an initial graph network, the atoms in the initial graph network are nodes, and the chemical bonds are the edges connecting the nodes; the random initialization vector is used to identify the weight vector of each node in the initial graph network; according to the connection relationship of the initial graph network reconstructs each node of the initial graph network to obtain a reconstruction graph network, and repeats the reconstruction steps to obtain at least two layers of the reconstruction graph network; according to the classification labels, the initial graph network and at least a two-layer reconstruction graph network are deep learned, and construct a drug screening model.

In one embodiment, when the computer program is executed by the processor, the initial graph network for drawing the drug protein and the small molecule based on the chemical formula includes: performing molecular docking between the drug protein and the small molecule based on traditional molecular dynamics to obtain the target molecule; based on the chemical formulas of target molecules, draw initial graph networks of drug proteins and small molecule.

In one embodiment, when the computer program is executed by the processor, the initial graph network for drawing the drug protein and the small molecule based on the chemical formula includes: based on the chemical formula, draw the initial graph network for the drug protein and the small molecule respectively, and the initial graph at this time is the network contains an initial graph network for drug proteins and an initial graph network for small molecule.

In one embodiment, when the computer program is executed by the processor, using a random initialization vector to identify the weight vector of each node in the initial graph network includes: select the value of (0, 1) interval by uniform distribution or normal distribution to generate the initialization vector, and assign it to the node as its weight vector.

In one embodiment, when the computer program is executed by the processor, reconstructing each node of the initial graph network according to the connection relationship of the initial graph network to obtain a reconstruction graph network, which includes: obtain the weight vector of each node and the associated weight vector of the associated node connected with the node according to the connection relationship of the initial graph network; integrate the weight vector with the associated weight vector to obtain the reconstruction weight vector of the node; generate the reconstruction graph network according to the reconstruction weight vector.

In one embodiment, when the computer program is executed by the processor, performing deep learning on the initial graph network and the at least two-layer reconstruction graph network according to the classification labels, and constructing the drug screening model, includes: respectively extract features of the initial graph network and at least two layers of the reconstruction graph network to obtain the hierarchical network features; according to the classification labels, the deep learning network is used to learn the hierarchical network features, and construct a drug screening model.

In one embodiment, when the computer program is executed by the processor, perform the feature extraction on the initial graph network and the at least two-layer reconstruction graph network, respectively, to obtain hierarchical network features, including: feature extraction is performed on the initial graph network and at least two layers of reconstruction graph networks by functions to obtain function vector features; the function vector features are normalized in the probability space to obtain hierarchical network features.

In one embodiment, a computer-readable storage medium is provided on which a computer program is stored, and the computer program implement the following steps when executed by a processor: drawing the target initial graph network based on the chemical formula of the target protein and the small molecule, the atoms in the initial graph network are nodes, and the chemical bonds are the edges connecting the nodes; input the target initial graph network into the drug screening model, and output the analysis results of protein and the small molecule, wherein the drug screening model is obtained by training by the above-mentioned method.

The embodiments described herein are only specific embodiments of the present application, and are not intended to limit the protection scope of the present application. Any modification or equivalent that can be easily conceived by persons skilled in the art should all fall within the protection scope of the present application. Therefore, the protection scope of the present disclosure is subject to the protection scope of the claims.

What is claimed is:

1. A drug screening model construction method, which is used for protein crystal structure screening, comprising:

obtaining a drug training set, wherein the drug training set comprises a chemical formula of a drug protein, a chemical formula of a small molecule, and a classification label;

based on the chemical formula, drawing an initial graph network of the drug protein and the small molecule, wherein atoms are nodes and wherein chemical bonds are edges connecting nodes;

using a random initialization vector to identify an initial weight vector of each node in the initial graph network;

reconstructing each node of the initial graph network according to the initial weight vector of the node, weight vectors of nodes connected to the node, and a connection relationship of the initial graph network to obtain a reconstruction network, repeating the reconstruction steps to obtain at least two layers of reconstruction networks;

respectively extracting hierarchical network features from the initial graph network and at least two layers of reconstruction graph networks; and constructing a drug screening model by performing deep learning on the hierarchical network features according to the classification labels.

2. The method according to claim 1, wherein the initial graph network for drawing the drug protein and small molecule based on chemical formulas further comprises:

performing molecular docking between the drug protein and the small molecule based on traditional molecular dynamics to obtain a target molecule; and according to a chemical formula of the target molecule, drawing the initial graph network of the drug protein and the small molecule.

3. The method according to claim 1, wherein, based on the chemical formula, the initial graph network for drawing the drug protein and the small molecule further comprises:

drawing the initial graph network of the drug protein and the small molecule based on the chemical formula, wherein the initial graph network includes the initial graph network of the drug protein and the initial graph network of the small molecule.

4. The method according to claim 1, wherein using the random initialization vector to identify the weight vector of each node in the initial graph network further comprises:

using at least one subset of a set comprising uniform distribution and normal distribution to select a value of (0, 1) interval to generate an initialization vector and assigning the initialization vector to a node as the weight vector.

5. The method according to claim 1, wherein reconstructing each node of the initial graph network according to the connection relationship of the initial graph network to obtain a reconstruction graph network, further comprises:

obtaining the weight vector of each node and the associated weight vector of the associated node connected with the node according to the connection relationship of the initial graph network;

integrating the weight vector with the associated weight vector to obtain the reconstruction weight vector of the node; and generating the reconstruction graph network according to the reconstruction weight vector.

6. The method according to claim 1, wherein extracting the hierarchical network features further comprising:

performing feature extraction on the initial graph network and at least two layers of reconstruction graph networks by functions to obtain function vector features; and normalizing the function vector features in a probability space to obtain hierarchical network features.

7. The method according to claim 1, further comprising:

drawing a target initial graph network based on the chemical formula of the target protein and small molecule;

inputting the target initial graph network into the drug screening model, and outputting an analysis result of the target protein and small molecule.

8. A drug screening model reconstruction device, comprising:

a training set acquisition module, used to acquire a drug training set, wherein the drug training set includes a chemical formula of a target protein, a chemical formula of a small molecule, and a classification label;

a graph network drawing module, used to draw an initial graph network based on the chemical formula, in which atoms are nodes and chemical bonds are edges connecting nodes;

a vector identification module, used to identify a weight vector of each node in the initial graph network by using a random initialization vector;

a reconstruction module, used to reconstruct each node of the initial graph network according to an initial weight vector of the node, weight vectors of nodes connected to the node, and a connection relationship of the initial graph network to obtain a reconstruction graph network, and repeating the reconstruction steps to obtain at least two layers of reconstruction networks; and a model training module, used to respectively extract hierarchical network features from the initial graph network and at least two layers of reconstruction graph networks, and construct a drug screening model by performing deep learning on a hierarchical network features according to the classification label.

9. A computer-readable storage medium on which a computer program is stored, characterized in that, when the computer program is executed by a processor, the steps of a method comprising:

obtaining a drug training set, wherein the drug training set comprises a chemical formula of a drug protein, a chemical formula of a small molecule, and a classification label;

based on the chemical formula, drawing an initial graph network of the drug protein and the small molecule, wherein atoms are nodes and wherein chemical bonds are edges connecting nodes;

using a random initialization vector to identify an initial weight vector of each node in the initial graph network;

reconstructing each node of the initial graph network according to the initial weight vector of the node, weight vectors of nodes connected to the node, and a connection relationship of the initial graph network to obtain a reconstruction network, repeating the reconstruction steps to obtain at least two layers of reconstruction networks;

respectively extracting hierarchical network features from the initial graph network and the at least two layers of reconstruction graph networks; and constructing a drug screening model by performing deep learning on the hierarchical network features according to the classification labels.

* * * * *